(12) United States Patent
Li et al.

(10) Patent No.: US 12,383,643 B1
(45) Date of Patent: Aug. 12, 2025

(54) APPARATUS FOR TREATING NAIL PLATE OR SKIN USING PLASMA

(71) Applicant: JUBILEE INTERNATIONAL BIOMEDICAL CO., LTD., Taipei (TW)

(72) Inventors: Hui-Fang Li, Taipei (TW); Han-Chang Chou, Taipei (TW); Bo-Yi Yu, Taipei (TW); Sheng-Ya Lin, Taipei (TW); Xin-Qi Chen, Taipei (TW)

(73) Assignee: JUBILEE INTERNATIONAL BIOMEDICAL CO., LTD., Taipei (TW)

( * ) Notice: Subject to any disclaimer, the term of this patent is extended or adjusted under 35 U.S.C. 154(b) by 0 days.

(21) Appl. No.: 19/093,650

(22) Filed: Mar. 28, 2025

(30) Foreign Application Priority Data

Mar. 29, 2024 (TW) .................................. 113111951

(51) Int. Cl.
*A61L 2/14* (2006.01)

(52) U.S. Cl.
CPC ............. *A61L 2/14* (2013.01); *A61L 2202/11* (2013.01); *A61L 2202/16* (2013.01)

(58) Field of Classification Search
CPC ..... A61L 2/14; A61L 2202/11; A61L 2202/16
See application file for complete search history.

(56) References Cited

FOREIGN PATENT DOCUMENTS

| CN | 102711909 B | 9/2015 |
|---|---|---|
| CN | 109731226 A | 5/2018 |

OTHER PUBLICATIONS

Taiwan Notice of Allowance mailed Jan. 23, 2025 in counterpart Taiwan application TW113111951, 2 pages in Chinese.
Taiwan Notice of Allowance mailed Jan. 23, 2025 in counterpart Taiwan application TW113111951, 2 pages in English.
Taiwan Office Action and Search Report mailed Aug. 26, 2024 in counterpart Taiwan application TW113111951, 10 pages in Chinese.
Taiwan Office Action and Search Report mailed Aug. 26, 2024 in counterpart Taiwan application TW113111951, 10 pages in English.

*Primary Examiner* — Sean E Conley
(74) *Attorney, Agent, or Firm* — Juan Carlos A. Marquez; Marquez IP Law Office, PLLC

(57) ABSTRACT

An apparatus for treating a nail plate or a skin using plasma is provided. The apparatus comprises a plasma generation assembly, a power supply, and a grounding electrode. The plasma generation assembly comprises a positive electrode module and a curved surface dielectric layer. The positive electrode module includes a discharging face. The curved surface dielectric layer includes a first surface and a second surface opposite to the first surface, wherein the first surface is adjacent to the discharging face, and clearances outside the second surface or holes from the first surface to the second surface are used for high frequency plasma generation. The clearances form a closed room. The power supply powers the plasma generation assembly so as to generate a current from the discharging face to the grounding electrode.

11 Claims, 10 Drawing Sheets

APPARATUS FOR TREATING NAIL PLATE OR SKIN USING PLASMA

CROSS-REFERENCE TO RELATED INVENTION

This patent application claims the benefit of Taiwan Application No. 113111951 filed Mar. 29, 2024, and the disclosure is incorporated herein by reference in its entirety.

BACKGROUND OF THE INVENTION

1. Field of the Invention

The present disclosure relates to a portable apparatus for generating plasma, in particular to a portable apparatus for treating user's nail plate or skin using plasma.

2. Description of Related Art

Plasma is the fourth fundamental state of matter after solid, liquid and gas. It is defined as "a quasi-neutral substance of charged and neutral particles which exhibits collective behavior" by couples of textbooks. Flame, lightning, polar light and sun are common forms of plasma state. Generally, the external energy is applied to a certain gas and free electrons in space are then accelerated, and thus, the free electrons impact the gas to produce more charged particles, active particles and free radicals so as to generate plasma. To take a macroscopic view, the gas still remains in an electrically neutral state, and the gas would emit light during the ionization.

Plasma is widely used in semiconductor manufacturing industry, such as plasma coating and plasma etching, and is also widely applied in consumer electronics, such as plasma flat screen TV. Besides, plasma has expanded its application to the skin care market for the purpose of skin beauty, sterilization and/or treatment.

In addition, the tinea pedis is a highly contagious foot skin disease caused by pathogenic fungi. It sometimes causes the nail plates of toes or even the nail plate of fingers to be infected, which is commonly known as onychomycosis.

Onychomycosis is a difficult disease to cure because the fungus lives inside the nail plate. The main component of the nail is hardened keratin, which makes it difficult for the medicine to penetrate. Various techniques have been used to treat onychomycosis, including topical medicines, systemic medicines, electrical heating, light heating, and ultraviolet sterilization, but all of them have their own shortcomings or insufficient efficacy.

Therefore, it is desired to have another portable device that uses plasma to treat the nail plates or skins of the user, which can overcome the shortcomings of the prior art and solve the problem of insufficient therapeutic efficacy.

SUMMARY OF THE INVENTION

In view of the deficiency of the conventional devices for treating user's skin using plasma, the present application provides a device for treating user's skin using plasma designed to be safer and with high treatment efficiency.

In one aspect of the present disclosure, an apparatus for treating a nail plate or a skin using plasma is provided. The apparatus comprises a plasma generation assembly comprising a positive electrode module including a discharging face with an adjustable position and a curved surface dielectric layer including a first surface and a second surface opposite to the first surface, wherein the first surface is adjacent to the discharging face, and clearances outside the second surface or holes from the first surface to the second surface are used for plasma generation; a grounding electrode; and a power supply powering the plasma generation assembly so as to generate a current from the discharging face to the grounding electrode.

In yet another aspect of the present disclosure, the apparatus further includes a housing covering one side of the positive electrode module opposite the curved surface dielectric layer.

In another aspect of the present disclosure, the positive electrode module includes: a substrate having a plurality of openings; and a plurality of electrode rods respectively disposed in the plurality of openings and capable of respectively moving in response to the curved surface dielectric layer in relation to the plurality of openings, wherein a plurality of contact areas on the plurality of electrode rods adjacent to the first surface forms the discharging face.

In another aspect of the present disclosure, the positive electrode module further includes a plurality of compression springs, a first end portion of each of the plurality of compression springs is accordingly fixed in each of the plurality of openings, and a second end portion of each of the plurality of compression springs accordingly abuts each of the plurality of electrode rods.

In another aspect of the present disclosure, the positive electrode module further includes a plurality of sleeves, and the first end portion of each of the plurality of compression springs is accordingly fixed in each of the plurality of sleeves, and each of the plurality of sleeves is accordingly fixed in each of the plurality of openings, and each of the plurality of electrode rods moves linearly relative to each of the plurality of sleeves.

In yet another aspect of the present disclosure, the positive electrode module is a soft electrode layer.

In yet another aspect of the present disclosure, the curved surface dielectric layer is a flexible dielectric plate having a plurality of protrusions, a flexible dielectric plate having a plurality of holes, or a dielectric material weave layer.

In another aspect of the present disclosure, the thickness of the flexible dielectric plate or the thickness of the dielectric material weave layer ranges from 0.05 mm to 2 mm, and the heights of the plurality of protrusions or the depth of the plurality of holes ranges from 0.05 mm to 2 mm.

In another aspect of the present disclosure, the apparatus further includes a gas supply unit which delivers air, oxygen, nitrogen, helium, neon or argon into the plasma generation assembly.

In another aspect of the present disclosure, the ground electrode is a ground pad or a ground ring.

BRIEF DESCRIPTION OF THE DRAWINGS

In order to sufficiently understand the essence, advantages and the preferred embodiments of the present invention, the following detailed description will be more clearly understood by referring to the accompanying drawings.

DETAILED DESCRIPTION OF THE INVENTION

The following description shows the preferred embodiments of the present invention. The present invention is described below by referring to the embodiments and the figures. Thus, the present invention is not intended to be limited to the embodiments shown but is to be accorded the principles disclosed herein. Furthermore, that various modifications or changes in light thereof will be suggested to persons skilled in the art and are to be included within the spirit and purview of this application and scope of the appended claims.

Figure 1:
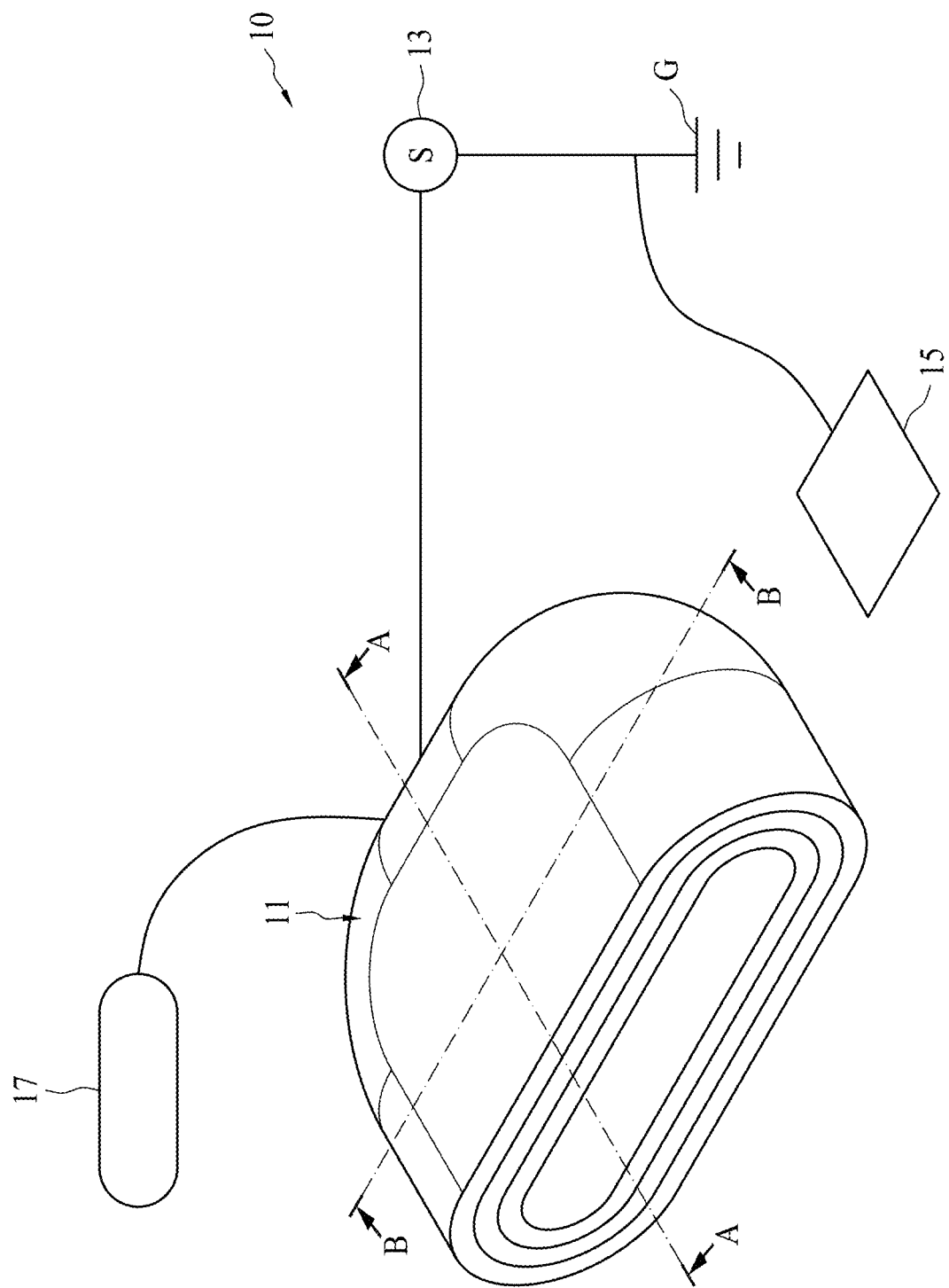
FIG. 1 depicts a schematic diagram of the appearance of a portable apparatus for treating a user's nail plate or skin using plasma according to the first embodiment of the present disclosure.

FIG. 1 depicts the first embodiment of the present disclosure, which shows a schematic diagram of the appearance of a portable apparatus for treating a user's nail plate or skin using plasma. The device 10 for treating a user's nail plates or skins using plasma includes a plasma generation assembly 11, a power supply 13, a grounding electrode 15, and a gas supply unit 17. The user can put hands or feet infected with bacteria or fungi into the inside of the plasma generation assembly 11 of the device 10, or the local skin that needs to be repaired can also be placed in the internal hermetic or partially hermetic room. This figure and related descriptions are only an example, and the appearance and size of the device 10 do not limit the scope of the claims of this application.

Figure 2:
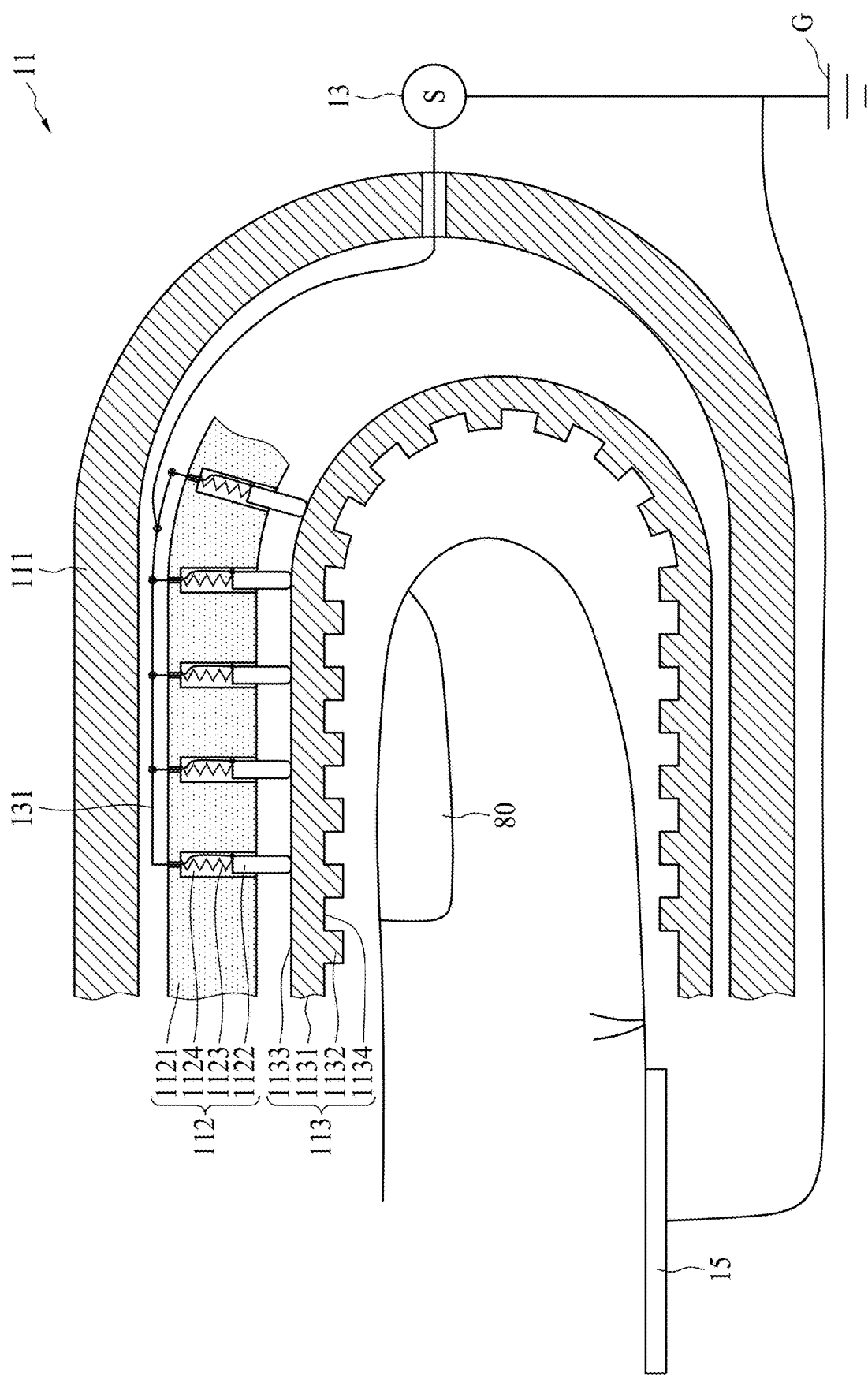
FIG. 2 depicts a schematic diagram of the internal structure along the section line A-A in FIG. 1 according to the first embodiment of the present disclosure.

Referring to FIG. 2, it is a schematic diagram of the internal structure along the section line A-A on the device 10 in FIG. 1. The nail plate 80 of one toe is put in the inside of the plasma generation assembly 11 of the device 10, and the grounding electrode 15 is closely attached to the sole of the foot. When the power supply 13 generates a high potential difference between the plasma generation assembly 11 and the grounding electrode 15, which is preferably between about 2 k V (Volt) and about 4.5 k V, more preferably between about 2.5 k V and about 4 k V, in order to generate plasma in the clearances above the nail plate 80. Air, nitrogen, oxygen, helium, neon, argon (inert gas) or mixed gases can be introduced into the clearances through the gas supply unit 17 to generate different plasmas to target the nail plate 80 or other portions of the skins. The plasmas accordingly have bactericidal, therapeutic and/or cosmetic effects thereon. The input port of the device 10 connected to the gas supply unit 17 can be designed to be similar to the pinhole on a basketball matched to an inflator or the inflation nozzle of a bicycle tire. The power supply 13 and the grounding electrode 15 are commonly connected to the ground G. Because the grounding electrode 15 is closely abutted upon the sole of the foot, this can prevent current from flowing to the heart, thereby avoiding the risk of affecting the heartbeat of a user. In addition, since the current loop is formed directly on the user's local skin, the intensity of the plasma is also quite high.

The plasma generation assembly 11 includes a housing 111, a positive electrode module 112 and a curved surface dielectric layer 113. The housing 111 covers the outside of the positive electrode module 112 opposite to the curved surface dielectric layer 113 so that the internal room is more airtight, and the therapeutic effect is enhanced.

Figure 3A:
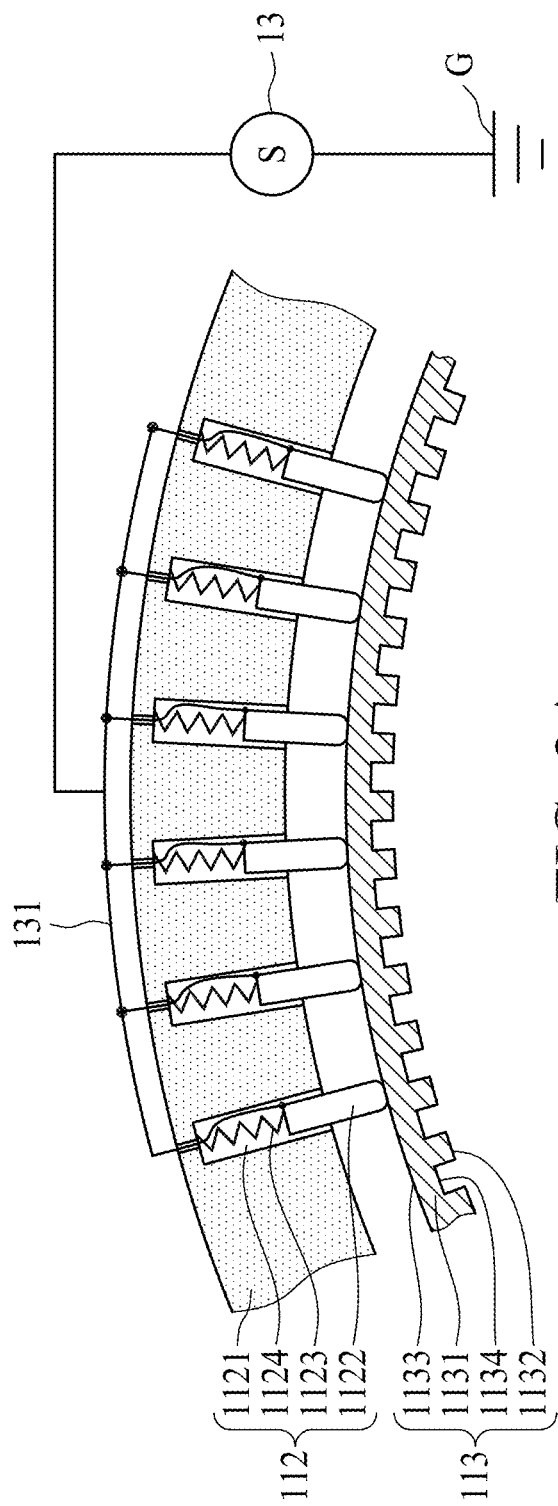
FIG. 3A depicts a schematic diagram of the partial internal structural along the section line B-B in FIG. 1 according to the first embodiment of the present disclosure.

Also, referring to FIG. 3A, this figure is a schematic diagram of the partial internal structural along the section line B-B in FIG. 1. The positive electrode module 112 includes a substrate 1121, electrode rods 1122, compression springs 1123 and openings 1124. The compression springs 1123 are embedded in the openings 1124 on the substrate 1121. Each electrode rod 1122 is respectively disposed in its corresponding opening 1124 and can move relative to the opening 1124. For example, the electrode rods 1122 can linearly slide within the holes in response to changes in the surface positions of the curved surface dielectric layer 113. The curved surface dielectric layer 113 includes a flexible dielectric plate 1131 and protrusions 1132 provided on the flexible dielectric plate 1131. Furthermore, the shape of the protrusions 1132 can be cylindrical as shown in this figure, or be conical, square columnar, semi-spherical, etc. The flexible dielectric plate 1131 includes a first surface 1133 and a second surface 1134 opposite to the first surface 1133, and the contact areas of the electrode rods 1122 adjacent to the first surface 1133 serve as a discharging face or electrode working surface. The power supply 13 supplies electrically power respectively through the metal wires 131 and produces potential differences between the electrode rods 1122 and the grounding electrode 15.

Figure 3B:
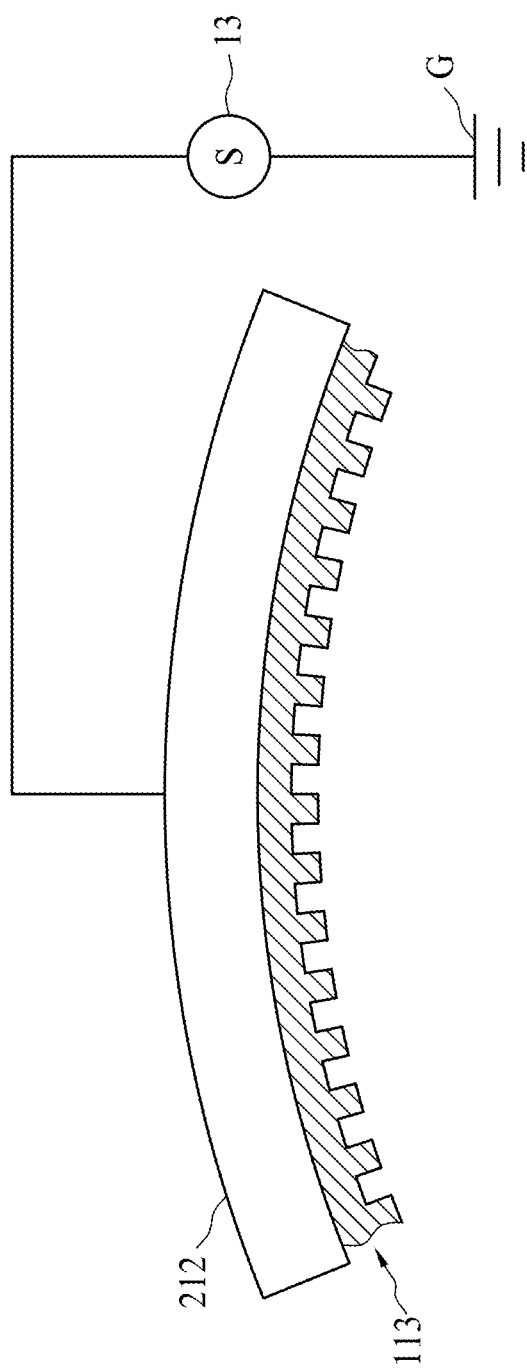
FIG. 3B depicts a schematic diagram of the partial internal structure along the section line B-B in FIG. 1 according to another embodiment of the present disclosure.
Figure 3C:
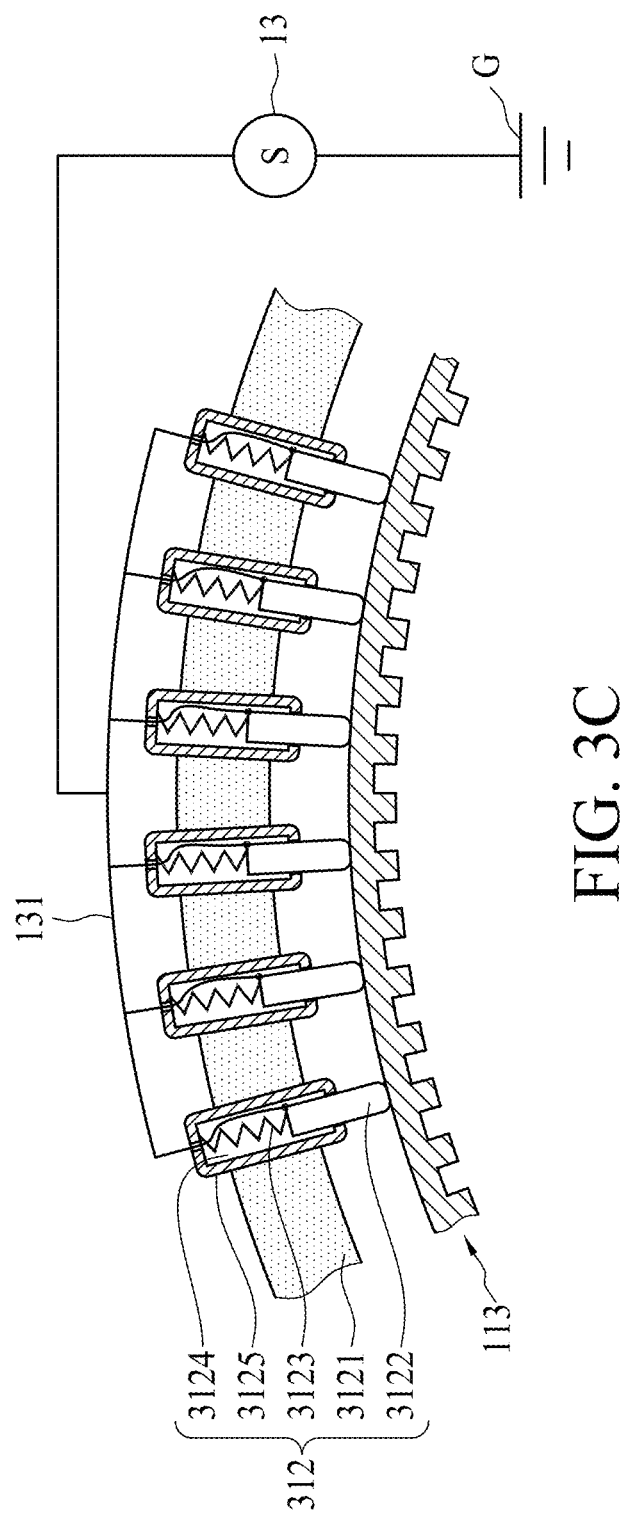
FIG. 3C depicts yet a schematic diagram of the partial internal structure along the section line B-B in FIG. 1 according to another embodiment of the present disclosure.

FIG. 3B depicts another embodiment of the present disclosure. The positive electrode module 212 is a soft electrode layer that is adaptive to changes in the surface positions of the curved surface dielectric layer 113 and in contact with each other. Compared with FIG. 3A, the positive electrode module 312 also includes a substrate 3121 and electrode rods 3122 (the outer diameter can be thinner, or the end face can be sharper), but the compression springs 3123 are respectively embedded in the sleeves 3125 within the openings 3124. That is, the sleeves 3125 are respectively fixed in the openings 3124, and each electrode rod 1122 has a linear motion relative to each sleeve 3125. Each compression spring 3123 can push against the end surface of each electrode rod 1122, whereby the electrode rods 3122 can contact the first surface 1133 of the flexible dielectric plate 1131.

Figure 4A:
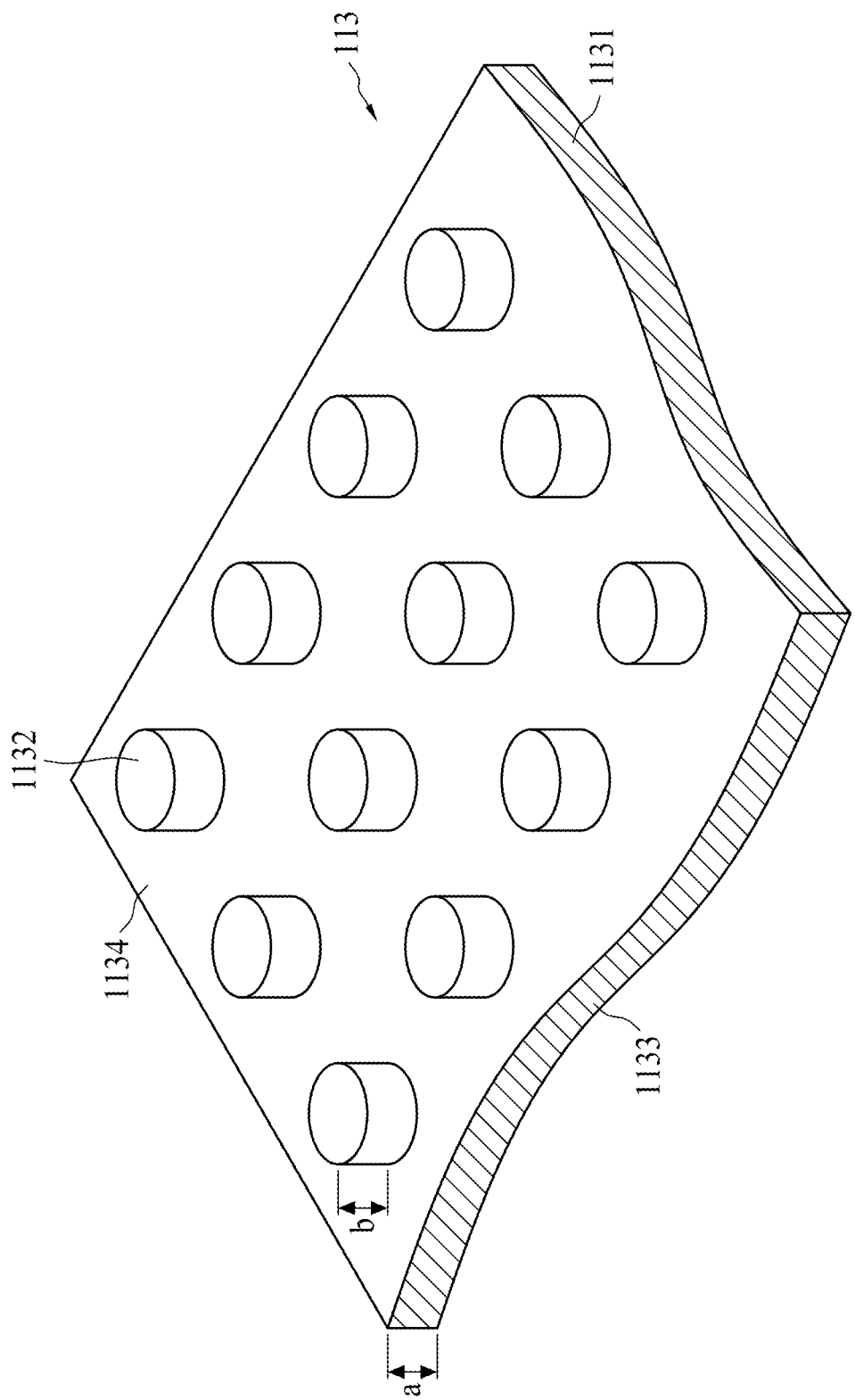
FIG. 4A depicts a schematic perspective view of the curved dielectric layer according to the first embodiment of the present disclosure.

FIG. 4A depicts a schematic perspective view of the curved dielectric layer according to the first embodiment of the present disclosure. The curved surface dielectric layer 113 includes a flexible dielectric plate 1131 and protrusions 1132 provided on the flexible dielectric plate 1131. Furthermore, the shape of the protrusions 1132 can be cylindrical as shown in this figure, or be conical, square columnar, semi-spherical, etc. There is gas in the clearances between the protrusions 1132. After the gas is dissociated by the electric field formed by the high potential difference between the electrode rods 1122 and the grounding electrode 15, positively charged gas molecules are generated to impact the nail plate or skin. In consideration of the properties of the insulator and the strength of the plasma, the thickness a of the flexible dielectric plate 1131 is in the range of 0.05 mm-2 mm, and the height b of the protrusions is in the range of 0.05 mm-2 mm.

Figure 4B:
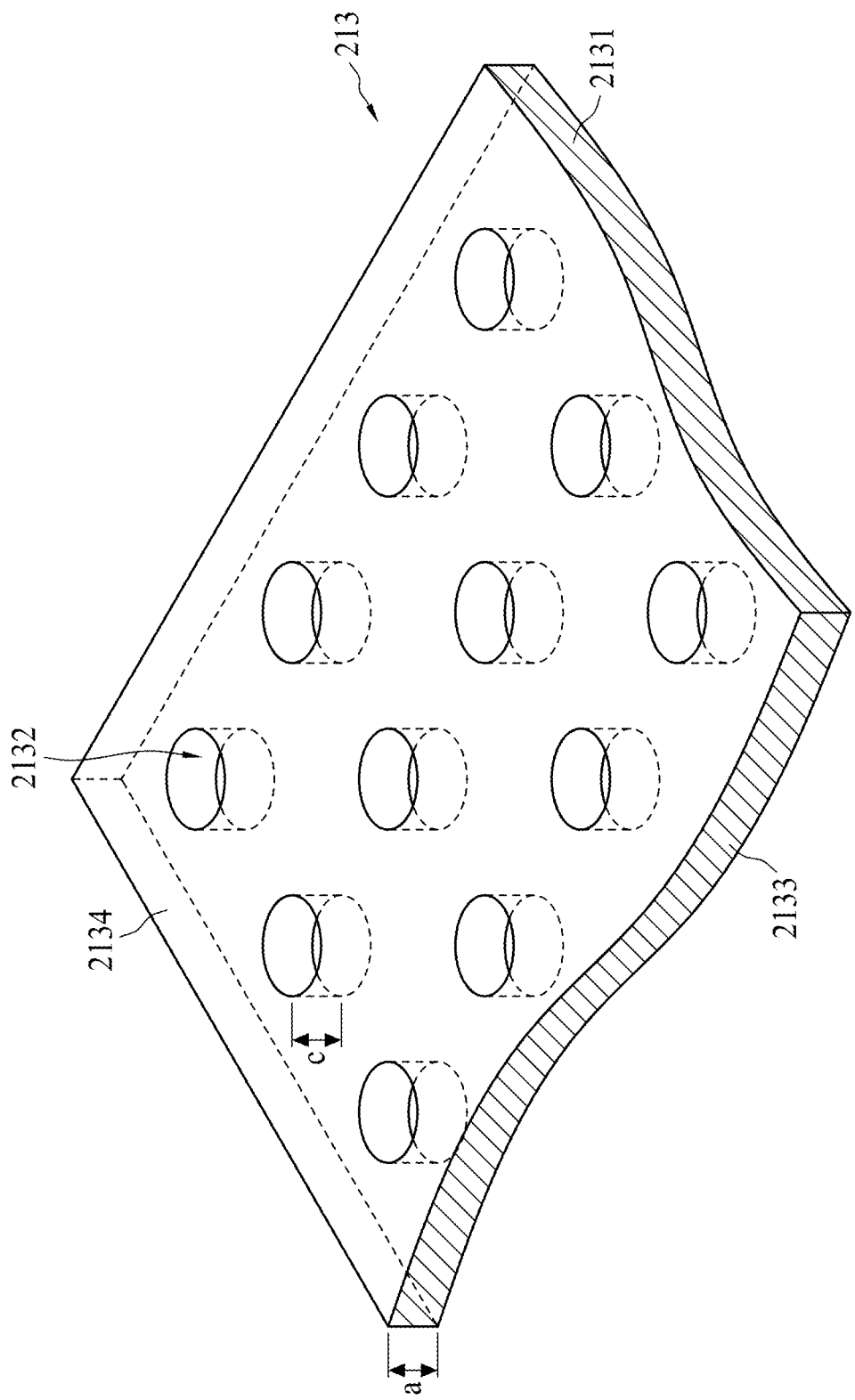
FIG. 4B depicts a schematic perspective view of a curved dielectric layer according to another embodiment of the present disclosure.

FIG. 4B depicts a schematic perspective view of a curved dielectric layer according to another embodiment of the present disclosure. The curved surface dielectric layer 213 includes a flexible dielectric plate 2131 and holes 2132 provided in the flexible dielectric plate 2131. Furthermore, the shape of the holes 2132 can be cylindrical or conical as shown in this figure, or be conical, square columnar, semi-spherical, etc. The depth a of the flexible dielectric plate 2131 is in the range of 0.05 mm-2 mm, and the depth c of the holes 2132 is in the range of 0.05 mm-2 mm. There is gas existing within the holes 2132. After the gas is dissociated by the electric field formed by the high potential difference between the electrode rods 1122 and the grounding electrode 15, positively charged gas molecules are generated to impact the nail plate or skin to achieve sterilization and cosmetic and/or therapeutic purposes.

Figure 4C:
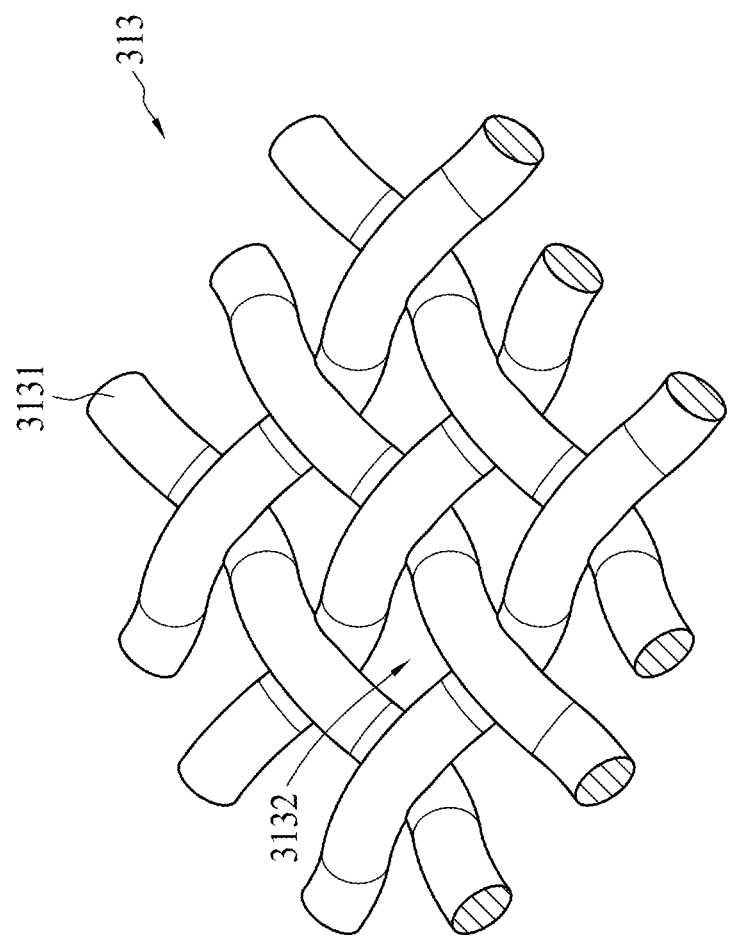
FIG. 4C depicts a schematic perspective view of a curved dielectric layer according to yet another embodiment of the present disclosure.

Different from FIGS. 4A and 4B, FIG. 4C depicts a schematic perspective view of a curved dielectric layer according to yet another embodiment of the present disclosure. The curved surface dielectric layer 313 includes a dielectric material weave layer 3131 and holes 3132 or pores disposed in the dielectric material weave layer 3131. The shape of the holes 3132 may be irregular as shown in this figure. Likewise, gases, such as oxygen, nitrogen, helium, neon or argon, are present in the holes 3132 and are dissociated by the electric field formed by the high potential difference between the electrode rods 1122 and the grounding electrode 15. Positively charged gas molecules are produced and impact the infected nail plate or skin to be repaired.

Figure 5:
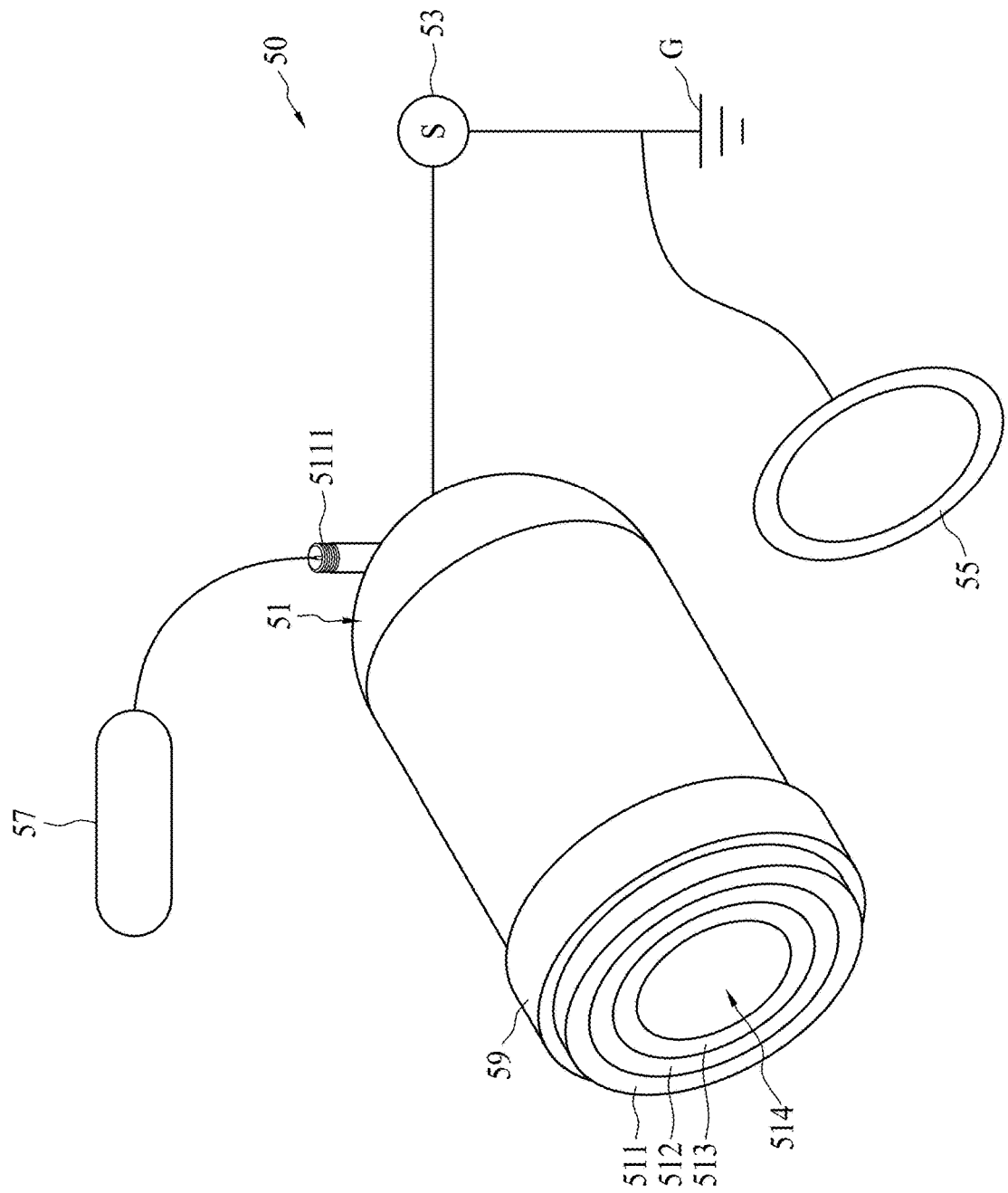
FIG. 5 depicts a schematic diagram of the appearance of a portable device for treating a user's nail plate or skin using plasma according to the second embodiment of the present disclosure.

FIG. 5 depicts a schematic diagram of the appearance of a portable device for treating a user's nail plate or skin using plasma according to the second embodiment of the present disclosure. The device 50 for treating a user's nail plate or skin using plasma includes a plasma generation assembly 51, a power supply 53, a grounding electrode 55, a gas supply unit 57 and a tightening member 59. The plasma generation assembly 51 is in the shape of a finger sleeve and has an inlet 514 that can accommodate a single finger to extend into its hermetic or partially hermetic room. The plasma generation assembly 51 includes a housing 511 with the inlet 514, a positive electrode module 512 and a curved surface dielectric layer 513. The grounding electrode 55 is an annular metal ring, which can be placed on the finger or wrist. The tightening member 59 surrounds the inlet 514 and exerts the housing 511 to reduce the dimension or size of the inlet 514 so that a better hermetic room can be formed inside to accommodate the finger. There is an inflation nozzle 5111 on the surface of the housing 511, which receives the gas delivery from the gas supply unit 57. The tightening member 59 may be an elastomer, such as a rubber band, used to shrink or constrain the size of the inlet 514.

The voltage and frequency of the power supply 53 or its output pulse power supply mode (duty cycle) can be adjusted to control the plasma intensity and power output. Accordingly, the plasma current is properly controlled to achieve sterilization, beautification, and/or other treatments for different purposes. In addition, since the plasma and current loop are formed directly on the user's skin or nail plate, active free radicals are directly generated and act on the skin without any retention and aging problems. Thus, the plasma effect will be quite significant.

Figure 6:
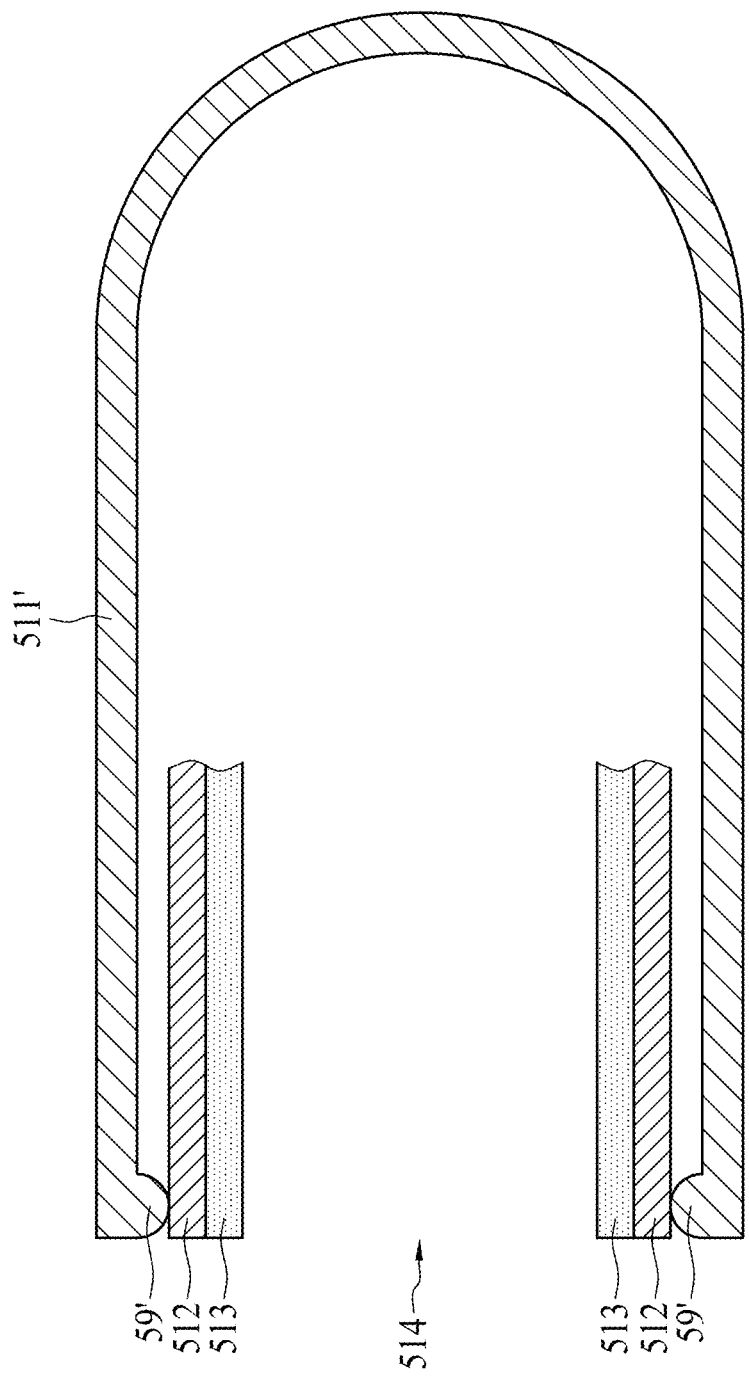
FIG. 6 is a schematic cross-sectional view of the modified housing and tightening member according to the second embodiment of the present disclosure.

FIG. 6 is a schematic cross-sectional view of the modified housing and tightening member according to the second embodiment of the present disclosure. In this modified embodiment, the fastening member 59' is integrated with the housing 511'. The fastening member 59' is similar to the flange or lip of the housing 511' and can be against the edges of the positive electrode module 512 and the curved surface dielectric layer 513 so that the surface of the inserted finger is firmly pressed to form a sealed internal room.

Although the present invention is written with respect to specific embodiments and implementations, various changes and modifications may be suggested to a person having ordinary skill in the art. It is intended that the present disclosure encompass such changes and modifications that fall within the scope of the appended claims.

What is claimed is:

1. An apparatus for treating a nail plate or a skin using plasma, comprising:
   a plasma generation assembly, comprising:
      a positive electrode module including a discharging face with an adjustable position, including:
         a substrate having a plurality of openings; and
         a plurality of electrode rods respectively disposed in the plurality of openings and capable of respectively moving in response to a curved surface dielectric layer in relation to the plurality of openings, wherein a plurality of contact areas on the plurality of electrode rods adjacent to a first surface forms the discharging face; and
      a curved surface dielectric layer including the first surface and a second surface opposite the first surface, wherein the first surface is adjacent to the discharging face, and clearances among a plurality of protrusions provided on the second surface are used for plasma generation;
   a grounding electrode coupled to the ground; and
   a power supply coupled to the positive electrode module and the grounding electrode so as to generate a current from the discharging face to the grounding electrode.

2. The apparatus according to claim 1, further comprising a housing covering one side of the positive electrode module opposite the curved surface dielectric layer.

3. The apparatus according to claim 1, wherein the positive electrode module further includes a plurality of compression springs, a first end portion of each of the plurality of compression springs is accordingly fixed in each of the plurality of openings, and a second end portion of each of the plurality of compression springs accordingly abuts each of the plurality of electrode rods.

4. The apparatus according to claim 3, wherein the positive electrode module further includes a plurality of sleeves, and the first end portion of each of the plurality of compression springs is accordingly fixed in each of the plurality of sleeves, and each of the plurality of sleeves is accordingly fixed in each of the plurality of openings, and each of the plurality of electrode rods moves linearly relative to each of the plurality of sleeves.

5. The apparatus according to claim 1, wherein the positive electrode module is a soft electrode layer.

6. The apparatus according to claim 1, wherein the curved surface dielectric layer is a flexible dielectric plate having the plurality of protrusions.

7. The apparatus according to claim 6, wherein a thickness of the flexible dielectric plate ranges from 0.05 mm to 2 mm, and heights of the plurality of protrusions ranges from 0.05 mm to 2 mm.

8. The apparatus according to claim 1, further comprising a gas supply unit which delivers air, oxygen, nitrogen, helium, neon or argon into the plasma generation assembly.

9. The apparatus according to claim 1, wherein the ground electrode is a ground pad or a ground ring.

10. The apparatus according to claim 2, further comprising a tightening member surrounding an inlet of the housing and exerting the housing to reduce a size of the inlet.

11. The apparatus according to claim 2, wherein the housing has an input port receiving delivered gas, and is designed to be an inflation pinhole or inflation nozzle.

\* \* \* \* \*